(12) United States Patent
Jadhav et al.

(10) Patent No.: US 12,721,992 B2
(45) Date of Patent: Sep. 1, 2026

(54) STABLE IV FLOW REGULATION CLAMP ASSEMBLY

(71) Applicant: CAREFUSION 303, INC., San Diego, CA (US)

(72) Inventors: Amarsinh Deeliprao Jadhav, Bangalore (IN); Rahul Malviya, Bangalore (IN); Narsi Reddy Sanikommu, Kanigiri (IN)

(73) Assignee: CAREFUSION 303, INC., San Diego, CA (US)

( * ) Notice: Subject to any disclaimer, the term of this patent is extended or adjusted under 35 U.S.C. 154(b) by 1055 days.

(21) Appl. No.: 17/831,237

(22) Filed: Jun. 2, 2022

(65) Prior Publication Data

US 2022/0409876 A1 Dec. 29, 2022

Related U.S. Application Data

(60) Provisional application No. 63/214,589, filed on Jun. 24, 2021.

(51) Int. Cl.
*A61M 39/28* (2006.01)

(52) U.S. Cl.
CPC .......... *A61M 39/287* (2013.01); *A61M 39/28* (2013.01); *A61M 39/283* (2013.01)

(58) Field of Classification Search
CPC .................. A61M 5/00; A61M 5/1418; A61M 2005/1652; A61M 5/16813; A61M 5/1401; A61M 39/283; A61M 2005/1401; A61M 39/287; A61M 5/16881; F16K 7/06
USPC .................................................... 604/250, 34
See application file for complete search history.

(56) References Cited

U.S. PATENT DOCUMENTS

| | | | | |
|---|---|---|---|---|
| 4,312,493 | A * | 1/1982 | Stauffer | A61M 39/283 251/8 |
| 4,337,791 | A | 7/1982 | Tech et al. | |
| 5,078,699 | A | 1/1992 | Haber et al. | |
| 8,313,081 | B2 | 11/2012 | Adelberg | |
| 8,544,815 | B2 | 10/2013 | Avery et al. | |
| 9,839,748 | B2 | 12/2017 | Ng et al. | |
| 2008/0083890 | A1 * | 4/2008 | Adelberg | F16K 7/066 251/6 |

(Continued)

FOREIGN PATENT DOCUMENTS

| | | | | |
|---|---|---|---|---|
| CN | 108159560 A | | 6/2018 | |
| JP | S6140567 U | | 3/1986 | |
| WO | WO-2012057602 A1 | * | 5/2012 | A61M 5/16881 |

OTHER PUBLICATIONS

International Search Report and Written Opinion for Application No. PCT/US2022/033478, dated Sep. 19, 2022, 13 pages.

(Continued)

*Primary Examiner* — Philip E Stimpert
(74) *Attorney, Agent, or Firm* — MASCHOFF BRENNAN

(57) ABSTRACT

A flow regulation clamp assembly for adjusting the fluid flow rate in a connector tube of an infusion set is provided. The flow regulation clamp assembly includes a housing to receive the connector tube, a slider slideably engaged within the housing and configured to compress the connector tube to provide a fluid flow adjustment, and a rotator knob moveable engaged with the housing and configured to move the slider. Infusion sets and methods of adjusting fluid flow rates are also provided.

20 Claims, 11 Drawing Sheets

(56) References Cited

U.S. PATENT DOCUMENTS

2014/0327759 A1* 11/2014 Tao ......................... G06T 7/262
348/135
2020/0324103 A1 10/2020 Pak et al.

OTHER PUBLICATIONS

Japanese Office Action for Application No. 2023-577334, dated Apr. 7, 2026, 4 pages including translation.

* cited by examiner

| Calculation to Find the Human Effort (Force) at the Knob to Operate | | | | 1400 | | | |
|---|---|---|---|---|---|---|---|
| Lead distance (pitch) = | 5 | mm | | | | | |
| Diameter of screw (d) = | 6 | mm | | | | | |
| Angle of slope = $\alpha$ | | | | | | | |
| Velocity ratio = VR | Displacement of load | | Xe = | Pi*d = | 18.84956 | = | 3.769911 |
| $VR = \frac{XE}{XL} = \frac{\pi D}{(La)_1}$ | Displacement of effort | | Xl = | 5 | | | |
| Efficiency of Screw = | tan $\alpha$ / tan ($\alpha$+$\beta$) | | | | | | |
| | | | | | | | |
| | | | | | | | |
| tan $\alpha$ = (pitch / pi *d) | $\alpha$ = tan-1(Pitch / pi *d) | = | 14.84 | Degrees | | | |
| $\alpha$ = | | | | | | | |
| $\beta$ =.35 (friction) | $\beta$ = tan-1 | = | 16.69 | Degrees | | | |
| | | | | | | | |
| Efficiency of screw $\eta$ = | tan $\alpha$ / tan ($\alpha$+$\beta$) | | 43.03178 | % | | | |
| | | | | | | | |
| Mechanical advantage = | V.R *$\eta$ | | 1.62226 | | | | |
| | | | | | | | |
| Mechanical advantage = | F (pinch the tube) / Fe | | | | | | |
| Fe = fl / Mechanical advantage | | | | | | | |
| Force required to pinch the tube | 30 | N | | | | | |
| Fe = fl / Mechanical advantage | | = | 18.49272 | | | | |
| | | | | | | | |
| Moment = | Force (fl) * Distance | = | 55.47816 | Nmm | | | |
| Diameter of knob = | 14 | mm | | | | | |
| | | | | | | | |
| Force on the knob end | 4.0 | N | | | | | |

FIG. 14

STABLE IV FLOW REGULATION CLAMP ASSEMBLY

CROSS-REFERENCES TO RELATED APPLICATIONS

This application claims the benefit of U.S. Provisional Patent Application No. 63/214,589 entitled "STABLE IV FLOW REGULATION CLAMP ASSEMBLY," filed on Jun. 24, 2021, the disclosure of which is hereby incorporated by reference in its entirety for all purposes.

TECHNICAL FIELD

The present disclosure generally relates to a gravity intravenous (IV) set or infusion pump flow control device, and in particular a stable IV flow regulation clamp assembly.

BACKGROUND

Flow controllers in the form of roller clamps are used in the medical field for IV applications. Roller clamps are found on standard administration sets and are attached during the manufacturing process. Typical roller clamps control a flow rate through an IV tube by clamping an IV tube in between a roller wheel and a housing, allowing the tube to be incrementally occluded by pinching the tubing as the roller clamp is tightened. Most roller clamps are easily regulated with one hand, where the preferred process is to completely close the roller clamp and regulate the rate by rolling the clamp upward to open it. The wheel of the roller clamp is maintained at its place because of transient fit with the roller body, engagement of tubing with the wheel and friction of wheel with the roller body. However, over a period at high flow rate the wheel tends to drift away from its set position and cause an inaccurate rate of fluid delivery.

Thus, it is desirable to provide a stable flow regulation clamp assembly that provides structural stability with the ability to control the flow consistently without variation in the adjusted flow rate.

SUMMARY

One or more embodiments provide a flow regulation clamp assembly. The flow regulation clamp assembly includes a housing having an open-ended boxlike structure and including a T-shaped housing channel disposed through a length of the housing and a knob base disposed on an outer portion of the housing and comprising a base bore extending through the knob base into the housing channel. The flow regulation clamp assembly also includes a slider disposed in the housing channel, the slider including a T-shaped slider housing configured to slidingly move along the T-shaped housing channel and a slider bore extending through at least a portion of the T-shaped slider housing. The flow regulation clamp assembly further includes a rotation knob coupled to the knob base, the rotation knob comprising an engagement member disposed through the base bore and received by the slider bore.

One or more embodiments provide an infusion set including a drip chamber, a connector tube and a flow regulation clamp assembly. The flow regulation clamp assembly includes a housing having an open-ended boxlike structure and including a T-shaped housing channel disposed through a length of the housing, wherein a base portion of the housing channel comprises two opposing side walls and a bottom wall that collectively define a tube channel configured to receive an intravenous tube, and a knob base disposed on an outer portion of the housing and comprising a base bore extending through the knob base into the housing channel. The flow regulation clamp assembly also includes a slider disposed in the housing channel, the slider including a T-shaped slider housing configured to slidingly move along the T-shaped housing channel and a slider bore extending through at least a portion of the T-shaped slider housing. The flow regulation clamp assembly further includes a rotation knob coupled to the knob base, the rotation knob comprising an engagement member disposed through the base bore and received by the slider bore.

One or more embodiments provide a method of operating a flow regulation clamp assembly. The method includes disposing an intravenous tube within a flow regulation clamp assembly by extending the intravenous tube through a length of a base portion of a T-shaped housing channel disposed within a housing; turning a rotation knob coupled to the housing in a first rotational direction, thus turning a threaded engagement member of the rotation knob in the first rotation direction, the threaded engagement member engaged with a threaded slider bore of a T-shaped slider disposed within the T-shaped housing channel; moving a base spar of the T-shaped slider downward into the base portion of the T-shaped housing channel a defined linear distance of travel associated with a degree of rotation of the rotation knob; and pushing a contact surface of the base spar into the intravenous tube the defined linear distance of travel, thus occluding the intravenous tube a defined amount associated with a defined reduced fluid flow rate through the intravenous tube.

The foregoing and other features, aspects and advantages of the disclosed embodiments will become more apparent from the following detailed description and accompanying drawings.

BRIEF DESCRIPTION OF THE DRAWINGS

The accompanying drawings, which are included to provide further understanding of the disclosure and are incorporated in and constitute a part of this specification, illustrate embodiments of the disclosure and together with the description serve to explain the principles of the disclosure.

FIG. 14 depicts a table of calculations of a flow regulation clamp assembly, according to aspects of the disclosure.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions are provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

Roller clamps are typically found on all standard administration sets and are attached during the manufacturing process. The roller clamp allows the tube to be incrementally occluded by pinching the tubing as the roller clamp is tightened. Most roller clamps are easily regulated with one hand. The preferred process is to completely close the roller clamp and regulate the rate as the clamp roller is rolled upward to open it. The clamp is designed to hold its place on the tubing, keeping the infusion rate constant between adjustments.

The wheel of the roller clamp is maintained at its place because of transient fit with the roller body, engagement of tubing with the wheel and friction of wheel with the roller body. Over a period at high flow rate the wheel drifts away from its set position and cause an inaccurate rate of fluid delivery to the patient.

Figure 1:
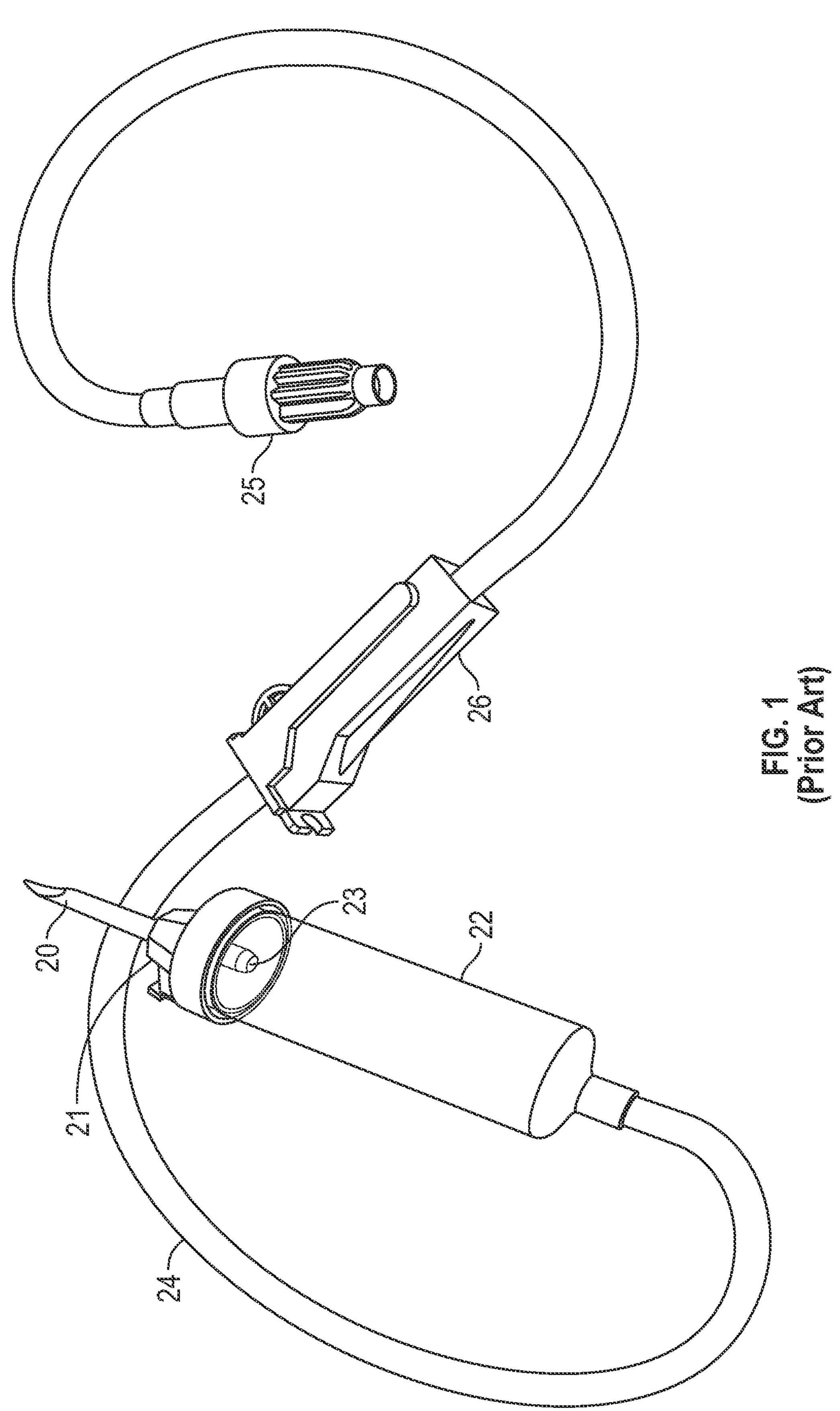
FIG. 1 depicts a perspective view of an example infusion set having a typical roller clamp.

The present disclosure relates to a flow regulator and in particular to a stable IV flow regulation clamp assembly for use in IV sets. The flow regulation clamp regulates the flow rate of a medical fluid (for example a solution of a drug to be administered to a patient, or blood) flowing through a tube. Typically, a standard infusion set is used to infuse the fluid. An example of a standard infusion set is shown in FIG. 1.

The infusion set includes a piercing spike 20 which may either be a sharp spike for piercing rubber stoppers or rounded and blunt for insertion into a bag. The spike contains one channel for fluid and optionally a second channel for venting. A vent 21 is usually present in the vicinity of the piercing spike to allow air to flow into the drip chamber 22. The vent 21 may be provided with a bacterial filter to prevent bacteria from entering the equipment.

The drip chamber 22 has a drop generator 23 at the top of the drip chamber 22 that produces drops of a certain size. Drops from the drop generator 23 fall into the drip chamber 22 such that the drip chamber 22 is partially filled with liquid. This prevents air bubbles from entering the connector tube 24, which would be harmful to a patient. A particle filter may be provided at the lower aperture of the drip chamber 22.

The connector tube 24 connects the drip chamber 22 with a recipient of the liquid (e.g., a container or a patient). The connector tube 24 is usually around 150 cm long and can be manufactured from PVC. The tube 24 is shown shortened in FIG. 1 for clarity. The connector tube 24 typically has a continuous diameter throughout the length of the tube.

At the end of the connector tube 24 is a Luer fitting 25 which is standardized for connection to all other pieces of apparatus having a standard Luer cone. The person skilled in the art will appreciate that the Luer fitting 25 can be fitted to a hypodermic needle (not shown) for infusing the medical fluid into a container or into the circulatory system of a patient (e.g., into a vein).

Between the drip chamber 22 and the Luer fitting 25 and engaging with the connector tube 24, is a roller clamp 26. The present disclosure is concerned with an improved roller clamp assembly, but a typical roller clamp 26 as known in the art will now be described for background information.

Figure 2:
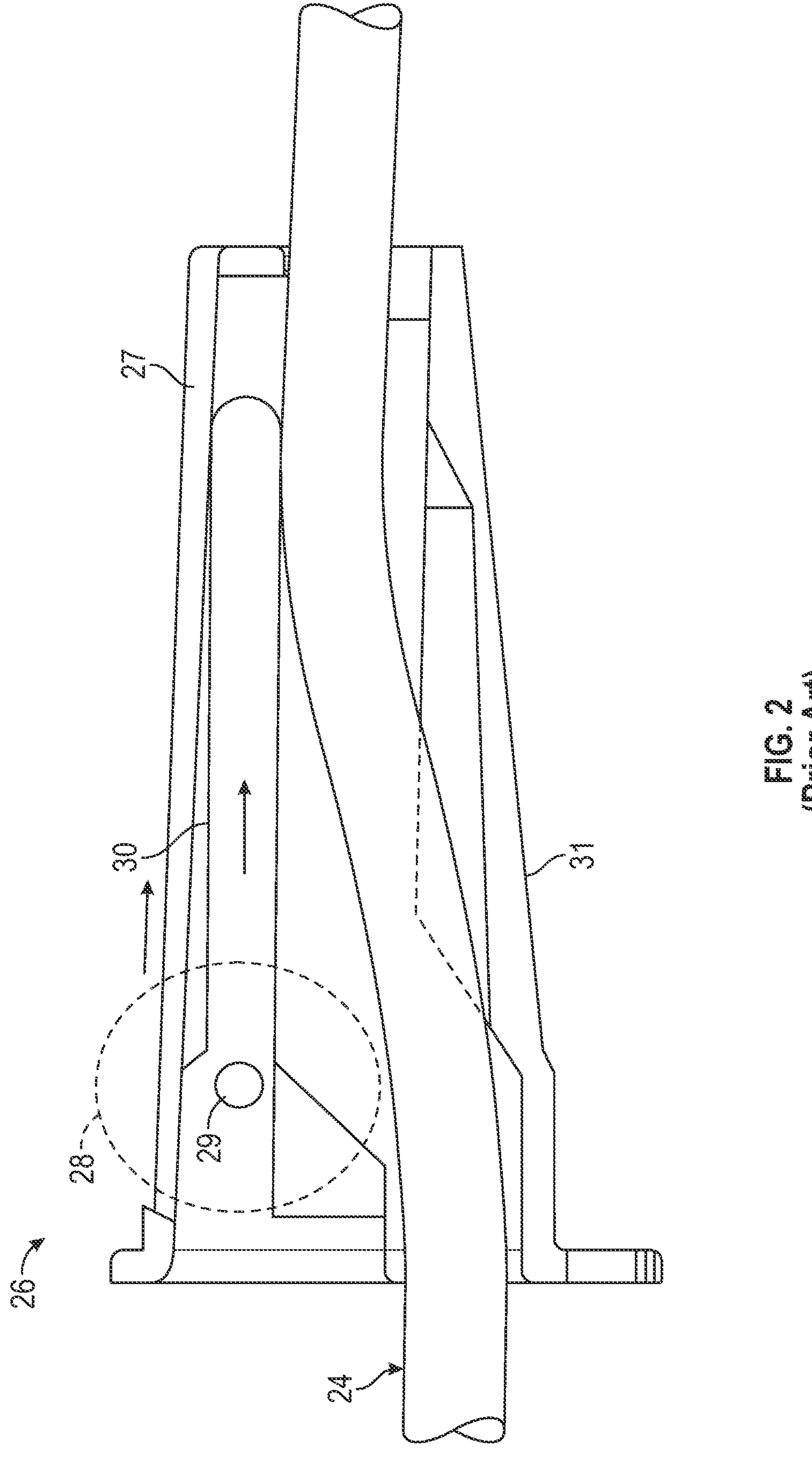
FIG. 2 depicts a cross-section side view of the roller clamp of FIG. 1.
Figure 3:
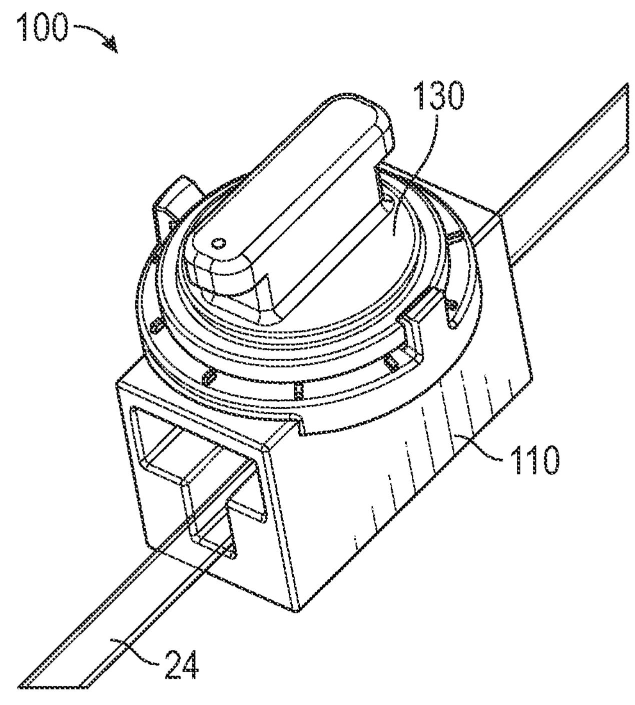
FIG. 3 depicts a perspective view of a flow regulation clamp assembly on an IV tube, according to aspects of the disclosure.
Figure 4:
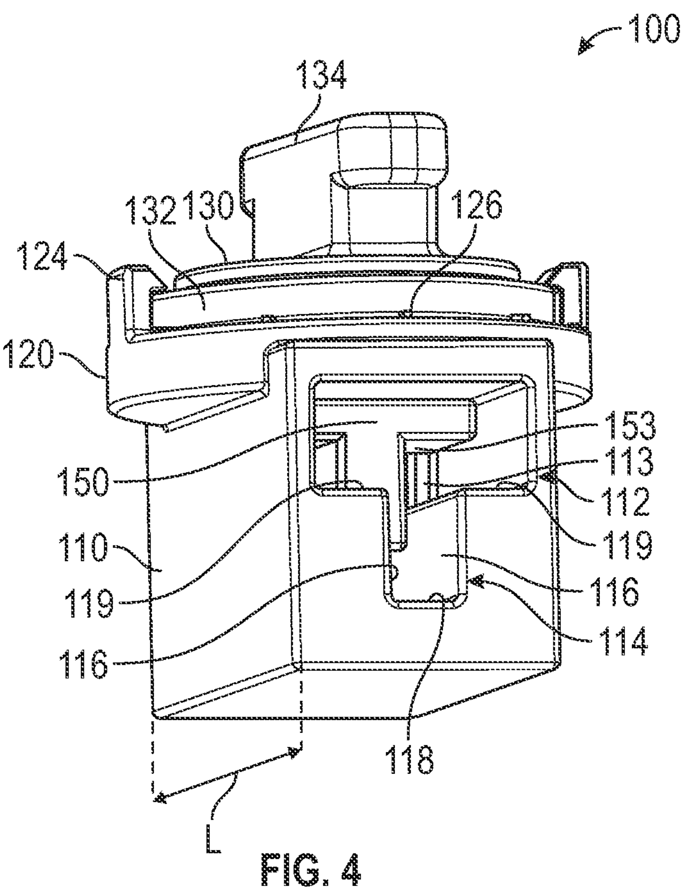
FIG. 4 depicts a perspective view of the flow regulation clamp assembly of FIG. 3, according to aspects of the disclosure.
Figure 5:
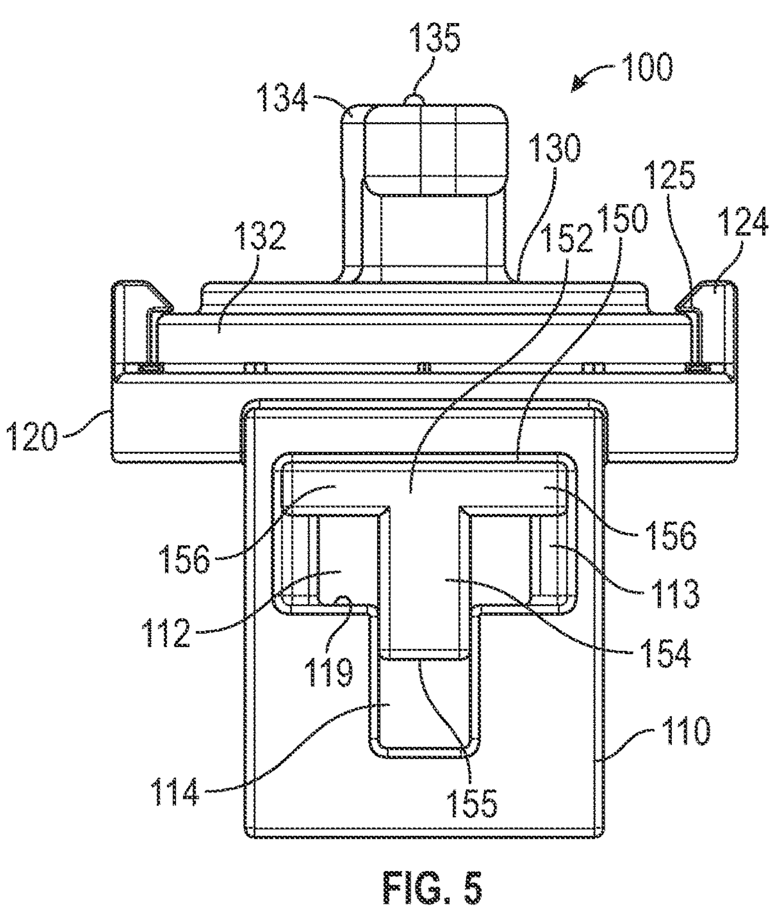
FIG. 5 depicts a front elevation view of the flow regulation clamp assembly of FIG. 3, according to aspects of the disclosure.
Figure 6:
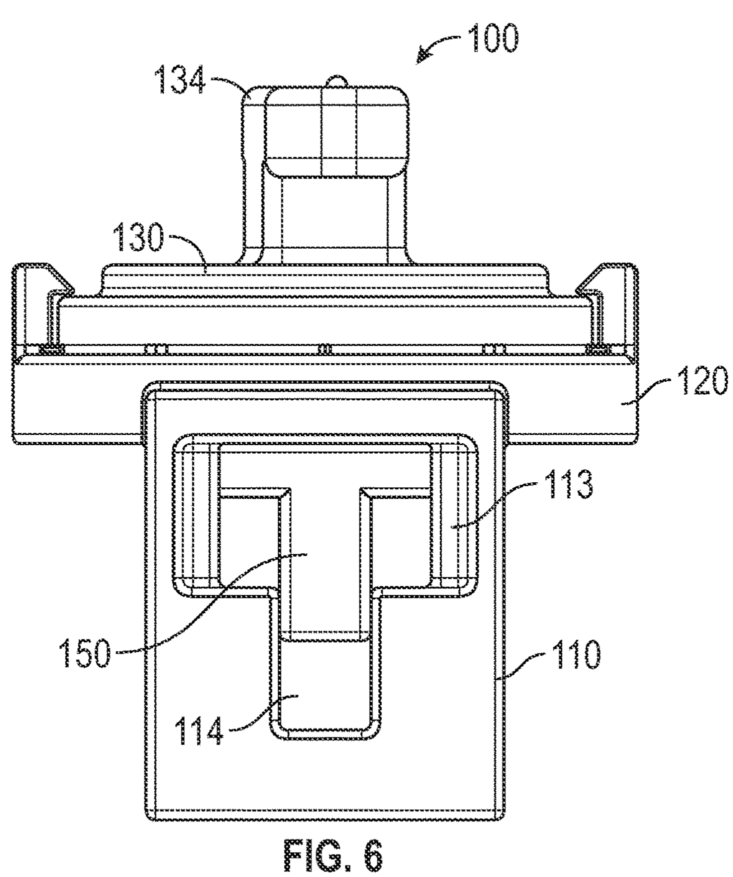
FIG. 6 depicts a rear view of the flow regulation clamp assembly of FIG. 3, according to aspects of the disclosure.

The roller clamp 26 illustrated in FIG. 2 has two opposing side walls 27 having a pair of guide grooves 30 that are aligned with each other and face each other. A flow-regulating roller 28 is provided having axially-projecting shafts 29 protruding from the centers of each side of the roller 28. The roller 28 is shown in outline for clarity. The shafts 29 of the roller 28 are captured by and seated in the guide grooves 30 so that the roller 28 can move up and down the guide grooves 30 as indicated by the arrows in FIG. 2.

The entire roller clamp 26 has four walls (see FIG. 1) in an open-ended boxlike construction and is dimensioned and configured to receive the connector tube 24. In use, the tube 24 passes through the roller clamp 26, between the two opposing side walls 27, the roller 28 and a guide wall 31 that is opposed to the roller 28.

In the roller clamp 26, the surface of the guide wall 31 converges along its length toward the position of the guide grooves 30 in the downward direction of the guide grooves 30 (e.g., in the direction of the arrows in FIG. 2). This tends to urge the connector tube 24 within the roller clamp 26 toward the guide grooves 30 and thus toward roller 28.

Thus, rolling the roller 28 downwardly along the guide grooves 30 in the direction of the gradually closer guide wall 31 in the direction of the arrows causes the roller 28 to impinge against the connector tube 24. As the roller 28 impinges on the tube 24, the tube 24 becomes squeezed, as it is a flexible material such as PVC, and the lumen of the infusion tube 24 therefore becomes smaller. In this way, by narrowing of the lumen, the flow rate of liquid passing through the connector tube 24 can be regulated.

Thus, the roller clamp 26 controls the flow rate through the infusion tube 24 by clamping the infusion tube 24 between the roller 28 and the guide wall 31. As discussed above, this provides for a course flow rate change because a small movement of the roller 28 causes a large change in the flow rate of the fluid through the tube 24. Also, the force of the fluid in the tube 24 exerts a biasing force against the roller 28, which often leads to slippage of the roller 28 (e.g., the roller 28 rolls back) from the adjusted position. Accordingly, it is desirable to have a flow regulation clamp design having structural stability with the ability to control the flow consistently without variation in adjusted flow rate.

With reference to FIGS. 3-12, a stable flow regulation clamp assembly 100 is shown. The flow regulation clamp assembly 100 includes a screw nut mechanism having a lower helix angle than a friction angle to provide improved control of flow regulation and a marking scale on a housing to assist in flow control. The flow regulation clamp assembly 100 has a housing 110, a rotation knob 130 and a slider 150.

The housing 110 has an open-ended boxlike construction and is dimensioned and configured to receive tubing, such as connector tube 24. A housing channel 112 may be configured as a T-shaped channel disposed through the entire length L of the housing 110. The bottom of the housing channel 112 defines a tube channel 114 having two opposing side walls 116 and a bottom wall 118. The tube channel 114 is configured to receive an IV tube such as tube 24. The housing channel 112 also includes two shelf surfaces 119 and a stop member 113.

The slider 150 has a T-shaped housing 152 configured to slidingly move in the housing channel 112. The housing 152 has a vertical spar 154 sized and shaped to fit into the tube channel 114 and two horizontal spars 156 each having a spar contact surface 153 configured to selectively engage with the shelf surfaces 119. A slider bore 158 in the housing 152 is disposed from a top surface 160 down into the housing 152. The slider bore 158 may extend all the way through the housing 152 or it may extend into only a portion of the housing 152. At least a portion of the length of the slider bore 158 is threaded and in some aspects of the disclosure the entire length of the slider bore 158 is threaded. A contact surface 155 of the vertical spar 154 is configured to come into contact with the tube 24.

Figure 7:
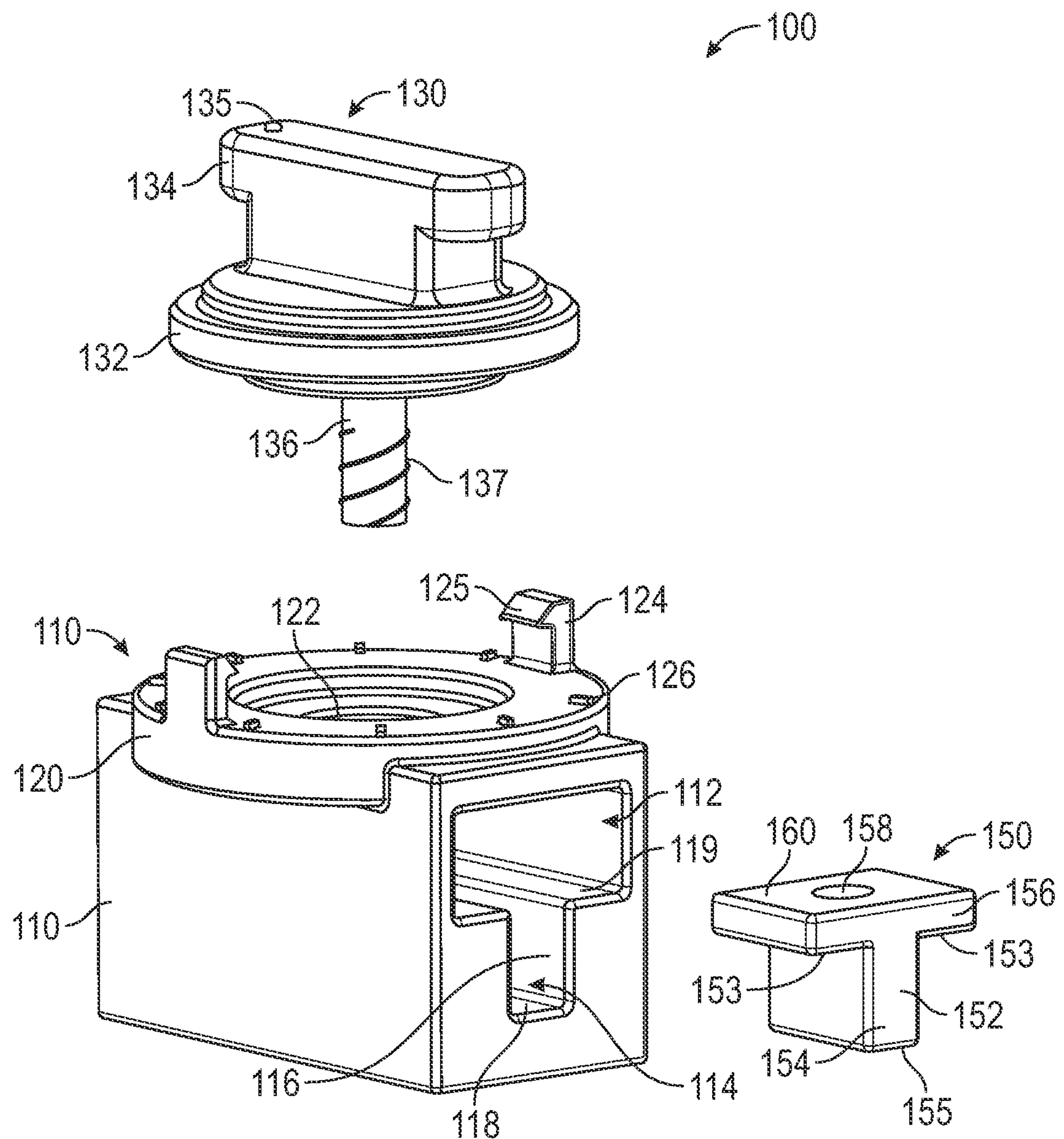
FIG. 7 depicts an exploded perspective view of the flow regulation clamp assembly of FIG. 3, according to aspects of the disclosure.
Figure 8:
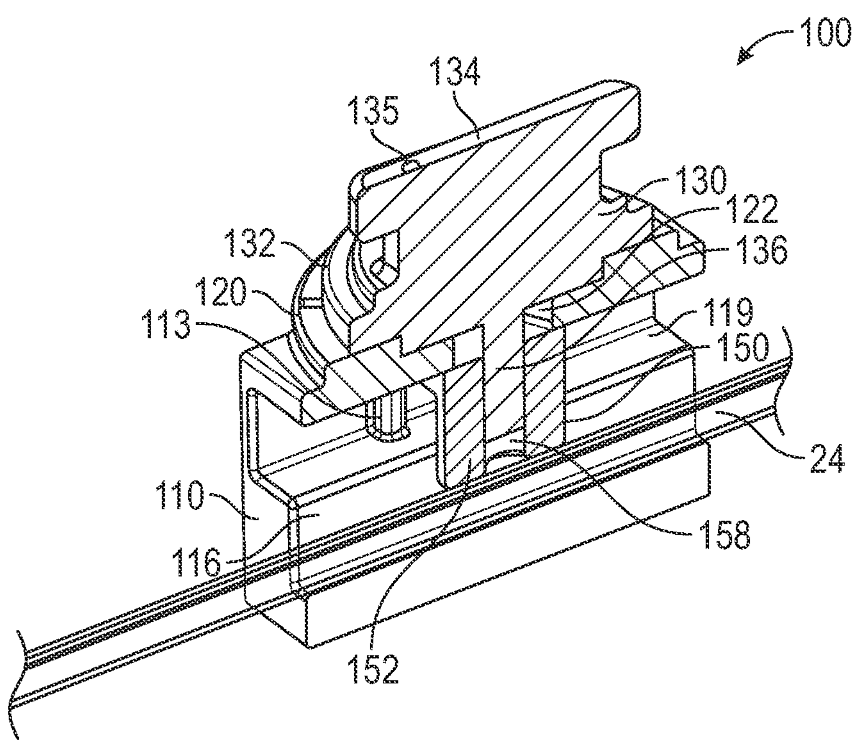
FIG. 8 depicts a cross-sectional perspective view of the flow regulation clamp assembly and tube of FIG. 3, according to aspects of the disclosure.
Figure 9:
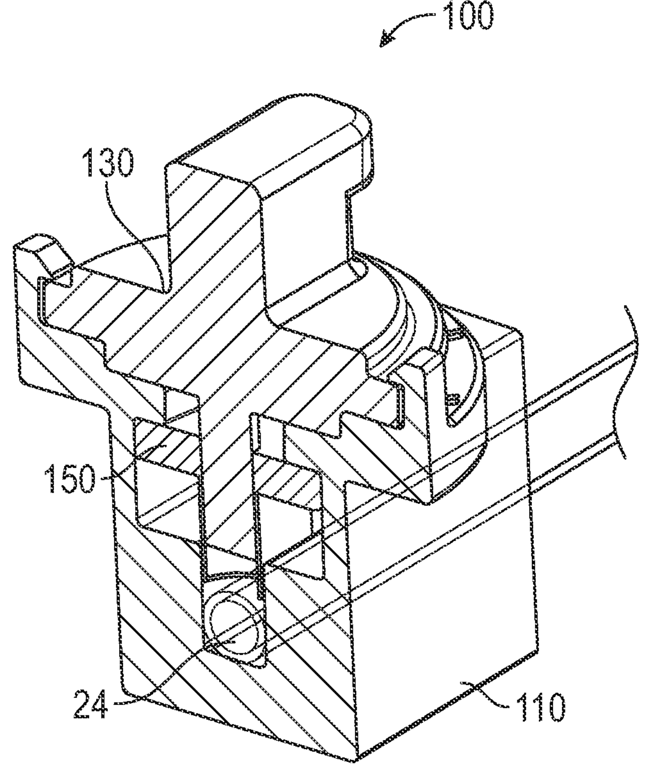
FIG. 9 depicts another cross-sectional perspective view of the flow regulation clamp assembly and tube of FIG. 3, according to aspects of the disclosure.
Figures 10, 11:
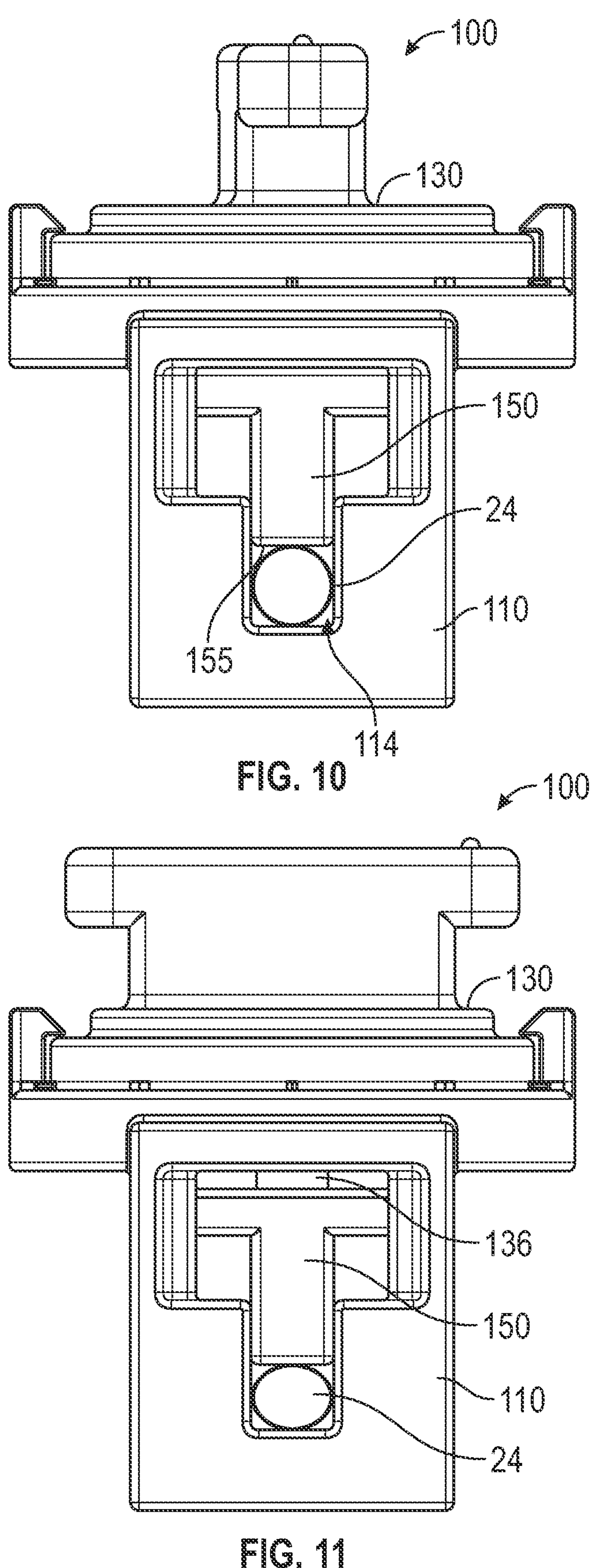
FIG. 10 depicts a rear view of the flow regulation clamp assembly and tube of FIG. 3 in an open flow position, according to aspects of the disclosure.
FIG. 11 depicts a rear view of the flow regulation clamp assembly and tube of FIG. 3 in a regulated flow position, according to aspects of the disclosure.
Figure 12:
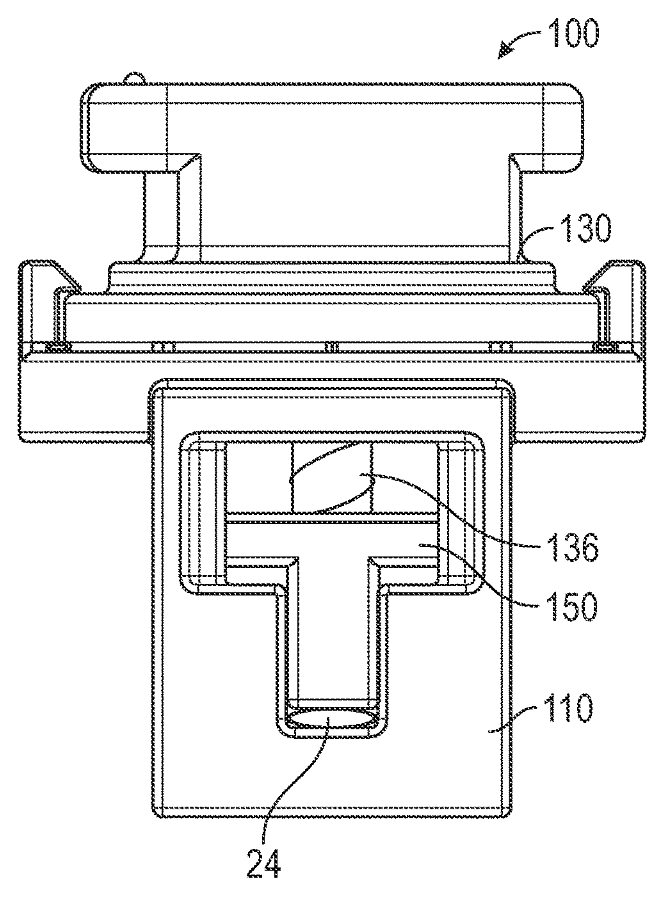
FIG. 12 depicts a rear view of the flow regulation clamp assembly and tube of FIG. 3 in a closed flow position, according to aspects of the disclosure.

The housing 110 further includes a knob base 120 configured to receive the rotation knob 130. The knob base 120 includes a base bore 122 extending through the knob base 120 into the housing channel 112. The knob base 120 also includes retention members 124 and scale markings 126. The knob base 120 may be any suitable shape, such as circular as shown in FIGS. 3-12. The scale markings 126 may be raised protrusions on the knob base 120 as shown in FIG. 7, or any other suitable marking (e.g., embossed, printed, etched).

The rotation knob 130 includes a base portion 132, a gripping portion 134 and an engagement member 136 (e.g., screw). The base portion 132 is sized and shaped to mate with the knob base 120. For example, as shown in FIGS. 3-12, the base portion 132 is circular in shape and has a smaller diameter than the diameter of the knob base 120. The retention members 124 of the knob base 120 are configured to engage with an outer perimeter of the base portion 132. For example, the depicted retention members 124 are opposing flexible clamps having securing portions 125 that overhang a portion of the base portion 132 (e.g., snap fit), thus movably securing the base portion 132 on the knob base 120. Thus, accidental disassembly of the rotator knob 130 from the housing 110 is unlikely, and assembly/reassembly of the rotator knob 130 and the housing 110 is easy due to the flexibility of the retention members 124.

The engagement member 136 is threaded and is sized and shaped to be disposed through the base bore 122 and received by the slider bore 158. The rotation knob may have a marker 135 (e.g., bump or mark) that provides a position indication. For example, the marker 135 may be disposed on a top end of the gripping portion 134 so that it may be visually aligned with any one of the scale markings 126.

In use, the tube 24 passes through the flow regulation assembly 100, between the two opposing side walls 116 and bottom wall 118 of the tube channel 114 and the bottom of the slider 150. Turning the rotation knob 130 in the appropriate direction (e.g., clockwise, counterclockwise) causes the threaded engagement member 136 to move within the threaded slider bore 158, causing the slider 150 (e.g., the bottom of the slider) to impinge against the tube 24. As the slider 150 impinges on the tube 24, the tube 24 becomes squeezed, as it is a flexible material such as PVC, and the lumen of the infusion tube 24 therefore becomes smaller. In this way, by narrowing of the lumen, the flow rate of liquid passing through the connector tube 24 can be regulated. The process may be reversed as well by turning the rotation knob 130 in the opposing direction, causing the slider 150 to move in a direction away from the tube 24 and decreasing the impingement of the tube 24.

Also in use, the gripping portion 134 of the rotation knob 130 may be aligned in a particular orientation according to the scale markings 126 on the knob base 120. Here, the scale markings 126 may indicate different levels of occlusion of the tube 24 associated with different fluid flow rates through the tube 24. For example, a 360 degree rotation of the rotation knob 130 may cause a specific linear length (e.g., X mm) of downward travel of the slider 150. Also, the contact area with the tube 24 may be the entire contact surface 155 of the vertical spar 154, where the contact surface 155 may be rectangular shaped, for example. According to aspects of the disclosure, the slider 150 may have any suitably shaped contact surface, such as a ball end to compress the tube 24 instead of a flat surface, for example.

In addition, by configuring the threading of the engagement member 136 and the threaded slider bore 158 such that the lead angle of the threading is less than the friction angle of the threading provides for the flow regulation assembly 100 to be self-locking. Thus, the slider 150 maintains its engagement position with the tube 24 during use (e.g., fluid flow in tube 24) because the frictional force between the engagement member 136 and the threaded slider bore 158 is greater than the helical sliding tendency between the engagement member 136 and the threaded slider bore 158 due to fluid forces pushing the tube 24 against the contact surface 155.

Further in use, the flow regulation assembly 100 may have different modes of operation. For example, an initial setting (e.g., factory setting) may have the rotation knob 130 in a clearance position where there is clearance between the tube 24 and the contact surface 155 of the slider 150. Here, the flow regulation assembly 100 can slide freely on the tube 24, allowing the flow regulation assembly 100 to be positioned at a desired location on the tube 24 (e.g., a set distance from a drip chamber 22). In a variety of intermediate use settings, the rotation knob 130 is rotated to adjust the fluid flow rate in the tube 24. As the rotation knob 130 is turned in a tightening direction (e.g., clockwise), the contact surface 155 of the slider 150 comes into contact with the tube 24 and proceeds to increasingly push into (e.g., occlude) the tube 24 as the rotation knob 130 continues to turn, thus further decreasing the fluid flow rate through the tube 24. In a closed setting, the rotation knob 130 is turned as far as necessary to cause the slider 150 to completely close (e.g., pinched closed) the tube 24 so that negligible or no fluid flows through the tube 24. Thus, the flow regulation assembly 100 is easy to operate, very stable while controlling the fluid flow rate in the tube 24 and provides for an accurate measurement of fluid flow compared to typical roller clamp designs.

The flow regulation assembly 100 may be easily assembled, according to aspects of the disclosure. For example, the housing 110 may be positioned in an assembly fixture (not shown) and the T-shaped slider 150 inserted into the T-shaped housing channel 112 until it contacts the stop member 113, which aligns the base bore 122 of the housing 110 and the slider bore 158 of the slider 150. Next, the rotation knob 130 may be placed on the knob base 120 so that the engagement member 136 is disposed through the base bore 122 and received by the slider bore 158. Then, the rotation knob 130 is rotated/turned in a tightening direction so that the threads 137, 157 of the engagement member 136 and the slider bore 158 become engaged enough to hold the flow regulation assembly 100 together. The flow regulation assembly 100 may then be slidingly mounted on a tube 24 as part of an IV set.

Each of the housing 110, rotation knob 130 and slider 150 may be integral one-piece components that are molded for efficient and low cost mass manufacturing, though any suitable manufacturing process may be used.

Figure 13:
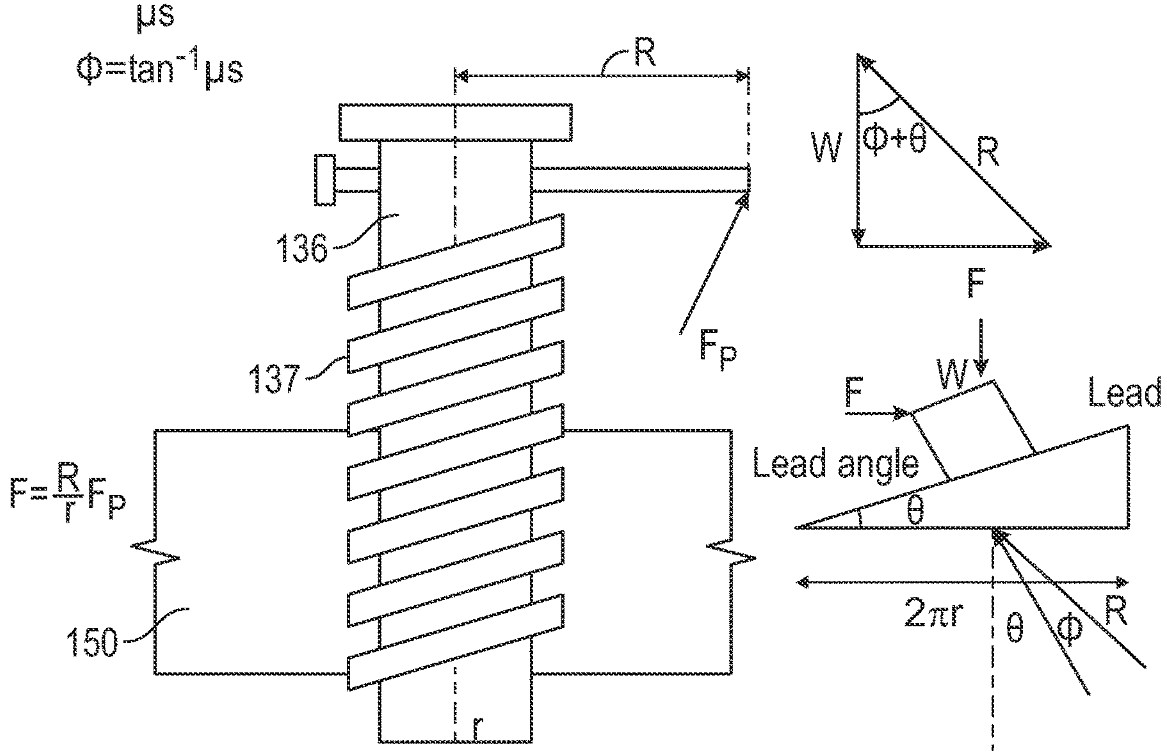
FIG. 13 depicts a schematic view of the flow regulation clamp assembly of FIG. 3, according to aspects of the disclosure.

As shown in FIG. 13, the engagement member 136 may have square threads 137 that are angled such the lead angle (e.g., helix angle) is less than the friction angle. Threads 157 of the slider bore 158 may also be square shaped to closely interact (e.g., tightly engage) with the square threads 137. The pitch of threads 137 may be configured such that one revolution of the rotation knob 130 is equal to the distance required for the slider 150 to move to compress the tube 24 fully closed. Due to the mechanical properties of the engagement member 136 and slider bore 158 (e.g., screw and nut), a small force applied to the rotation knob 130 will be converted to greater force compressing the tube 24 and a stabilized adjustment is achieved by self-locking of the engagement member 136/slider bore 158 combination. Also, one revolution (e.g., 360 degree rotation) of the rotation knob 130 provides a wide range to adjust the fluid flow in the tube 24.

As shown in FIG. 14, calculation chart 1400 shows sample calculations to determine the human effort (e.g., force) required at the rotation knob 130 to operate the flow regulation assembly 100. Here, the lead distance (e.g., pitch) is 5 mm, the diameter of the engagement member 136 is 6 mm and the angle of the slope is alpha. Thus, the displacement of effort Xe is pi times the diameter 6 mm to equal 18.84956 and the displacement of load Xl is 5. The velocity ratio VR is Xe divided by Xl (e.g., 18.84956/5) to equal 3.769911. The efficiency of the screw n equals the tangent of alpha divided by the tangent of alpha plus beta, where alpha equals the inverse tangent of the division of pitch by the product of pi times the diameter (e.g., alpha equals 14.84 degrees) and beta equals 0.35 times friction (e.g., beta equals 16.69 degrees). Thus, the efficiency of the screw here is 43.03178 percent, which leads to the mechanical advantage of the velocity ration VR times the efficiency of the screw n equaling 1.62226. Having the force required to pinch the tube of 30N yields a moment of force times the distance that equals 55.47816 Nmm. Given a diameter of the rotation knob 130 of 14 mm yields a calculated force on the knob end to be 4N.

Figures 15, 16:
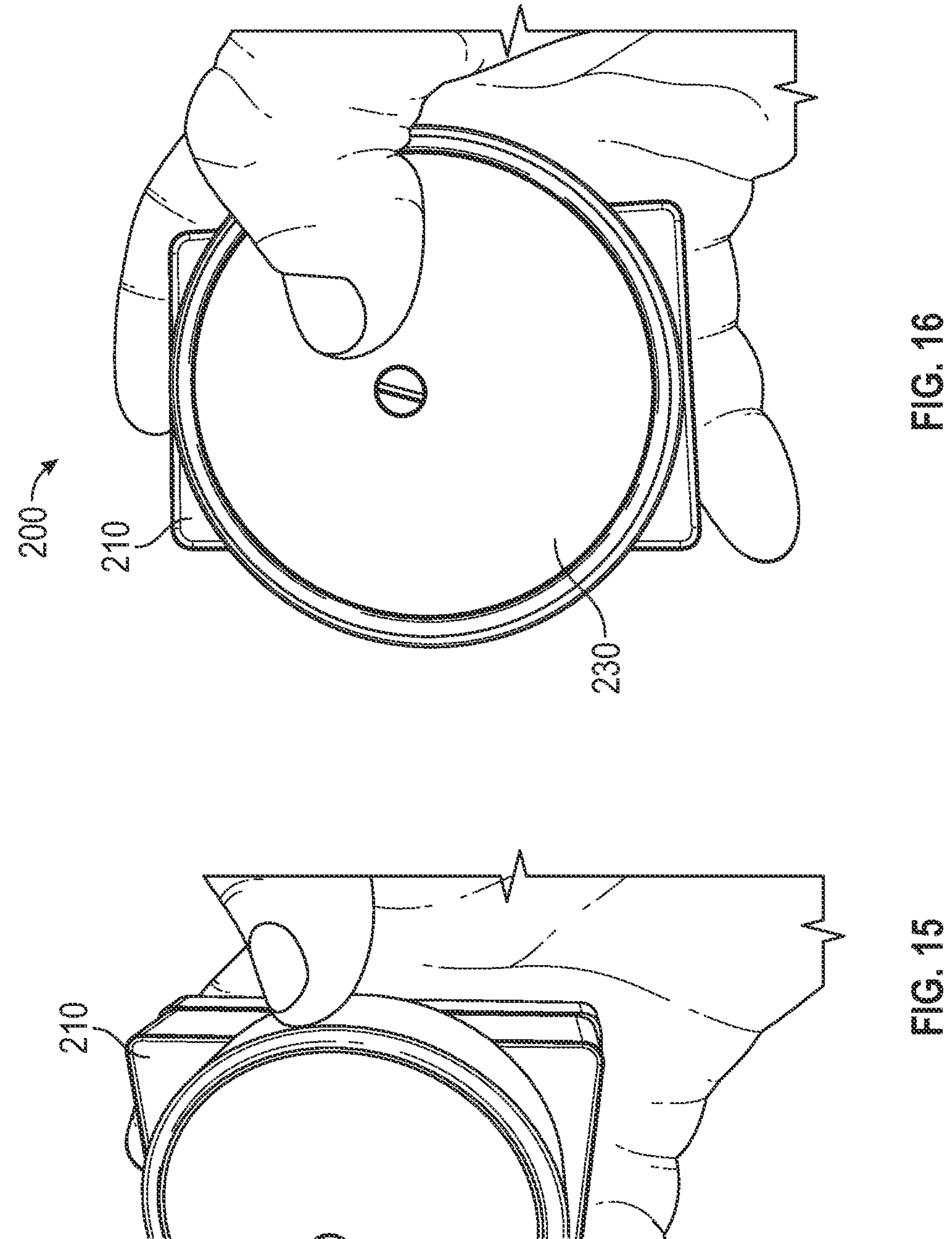
FIG. 15 depicts a perspective view of a one handed operation of a flow regulation clamp assembly, according to aspects of the disclosure.
FIG. 16 depicts a perspective view of another one handed operation of the flow regulation clamp assembly of FIG. 15, according to aspects of the disclosure.

With reference to FIGS. 15 and 16, an example of one handed operation of a flow regulation clamp assembly 200 is shown. Here, a housing 210 of the flow regulation clamp assembly 200 is held in the palm of a user's hand and a rotation knob 230 (e.g., circular disk with outer serrations) is moved/rotated by the user's thumb. As shown in FIG. 15, the thumb may engage the side of the rotation knob 230 and as shown in FIG. 16 may engage the top surface of the rotation knob 230.

Figure 17:
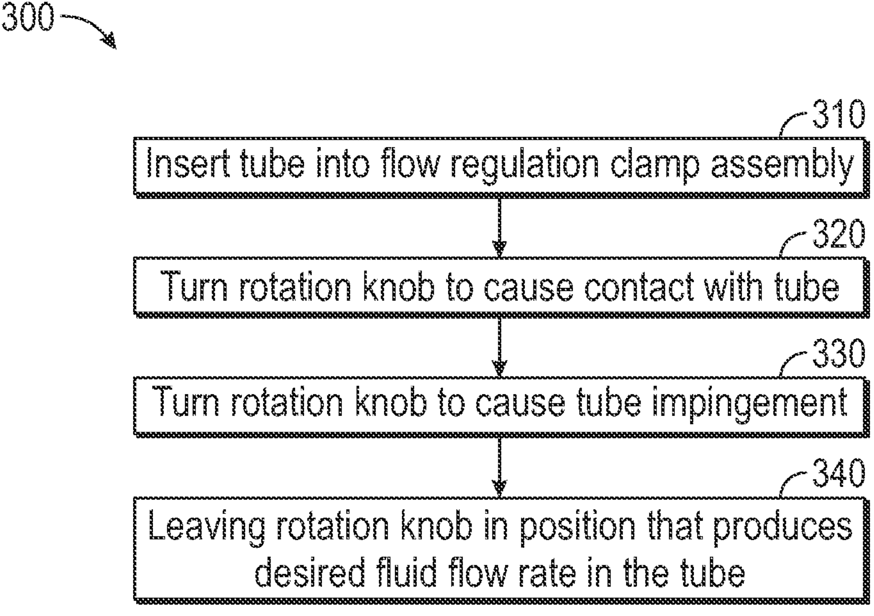
FIG. 17 depicts a schematic flow of a method of operating a flow regulation clamp assembly with an IV tube, according to aspects of the disclosure.

With reference to FIG. 17, a method 300 of operating a flow regulation clamp assembly is provided. In step 310, tubing (e.g., tube 24) is placed or disposed in a flow regulation clamp assembly (e.g., flow regulation clamp assembly 100) with the flow regulation clamp assembly in an open flow position (e.g., slider 150 not contacting the tube 24 or contacting but not impinging the tube 24). An adjustment knob (e.g., rotation knob 130) is turned/rotated to cause the tube to be contacted by a portion of the flow regulation clamp assembly (e.g., contact surface 155 contacts tube 24), in step 320. In step 330, the adjustment knob is turned/rotated further to occlude the tube to cause tube impingement to reach a desired fluid flow rate (e.g., the slider 150 impinges tube 24 to restrict the interior volume of the tube 24). When the desired fluid flow rate is achieved, the adjustment knob is left in place without the need for locking or securing members (e.g., frictional force between engagement member threads 137 and slider bore threads 157 keeps slider 150 in place), in step 340.

In one or more embodiments according to the disclosure, a flow regulation clamp assembly comprises: a housing having an open-ended boxlike structure and comprising: a T-shaped housing channel disposed through a length of the housing; and a knob base disposed on an outer portion of the housing and comprising a base bore extending through the knob base into the housing channel; a slider disposed in the housing channel, the slider comprising: a T-shaped slider housing configured to slidingly move along the T-shaped housing channel; and a slider bore extending through at least a portion of the T-shaped slider housing; and a rotation knob coupled to the knob base, the rotation knob comprising an engagement member disposed through the base bore and received by the slider bore.

In aspects of the disclosure, a base portion of the T-shaped housing channel comprises two opposing side walls and a bottom wall that collectively define a tube channel configured to receive an intravenous tube. In aspects of the disclosure, the T-shaped slider housing comprises a base spar configured to slidingly fit into the tube channel, the base spar comprising a contact surface configured to engage the intravenous tube. In aspects of the disclosure, the T-shaped housing channel comprises a top portion comprising two shelf surfaces extending outward from the base portion. In aspects of the disclosure, the T-shaped slider housing comprises two top spars each comprising a spar contact surface configured to selectively engage with one of the two shelf surfaces. In aspects of the disclosure, a height of each of the two top spars is less than a height of the top portion of the T-shaped housing channel, and wherein the T-shaped slider housing is configured to move up and down within the T-shaped housing channel.

In aspects of the disclosure, the T-shaped housing channel comprises a stop member configured to: prevent the T-shaped slider from slidably moving further along the T-shaped housing channel; and to align the base bore and the slider bore. In aspects of the disclosure, the knob base comprises at least one retention member configured to engage with a base portion of the rotation knob to keep the rotation knob movably coupled to the knob base. In aspects of the disclosure, the at least one retention member comprises opposing flexible clamps each having a securing portion that overhangs a portion of the base portion of the rotation knob. In aspects of the disclosure, the knob base comprises a plurality of scale markings disposed on a viewable surface of the knob base, the scale markings configured to indicate levels of occlusion of an intravenous tube disposed within the T-shaped housing channel, each level of occlusion associated with a fluid flow rate through the intravenous tube.

In aspects of the disclosure, each of the engagement member of the rotation knob and the slider bore is threaded, wherein rotation of the engagement member in a first direction within the slider bore causes the T-shaped slider housing to move upward within the T-shaped housing channel, and wherein rotation of the engagement member in a second direction within the slider bore causes the T-shaped slider housing to move downward within the T-shaped housing channel. In aspects of the disclosure, a specific degree of rotation of the rotation knob in the first direction is configured to cause upward travel of the T-shaped slider housing a specific linear distance, and wherein the specific degree of rotation of the rotation knob in the second direction is configured to cause downward travel of the T-shaped slider housing the specific linear distance.

In aspects of the disclosure, threading of each of the engagement member and the slider bore comprises square shaped threads configured so that a lead angle of the threading is less than a friction angle of the threading. In aspects of the disclosure, the slider is configured to be self-locking by maintaining an engagement position against an intravenous tube disposed within the T-shaped housing channel based on a frictional force between the engagement member and the slider bore being greater than a helical sliding tendency between the engagement member and the slider bore due to fluid forces pushing the intravenous tube against the slider. In aspects of the disclosure, a pitch of the square shaped threads is configured so that one revolution of the rotation knob equates to a linear distance required for the slider to move downward to compress an intravenous tube fully closed.

In one or more embodiments according to the disclosure, an infusion set comprises a drip chamber; a connector tube and a flow regulation clamp assembly comprising: a housing having an open-ended boxlike structure and comprising: a T-shaped housing channel disposed through a length of the housing, wherein a base portion of the housing channel comprises two opposing side walls and a bottom wall that collectively define a tube channel configured to receive an intravenous tube; and a knob base disposed on an outer portion of the housing and comprising a base bore extending through the knob base into the housing channel; a slider disposed in the housing channel, the slider comprising: a T-shaped slider housing configured to slidingly move along the housing channel; and a slider bore extending through at least a portion of the slider housing; and a rotation knob coupled to the knob base, the rotation knob comprising an engagement member disposed through the base bore and received by the slider bore.

In aspects of the disclosure, each of the engagement member of the rotation knob and the slider bore comprises square shaped threads configured so that a lead angle of the threading is less than a friction angle of the threading, wherein the slider is configured to be self-locking by maintaining an engagement position against the intravenous tube based on a frictional force between the engagement member and the slider bore being greater than a helical sliding tendency between the engagement member and the slider bore due to fluid forces pushing the intravenous tube against the slider. In aspects of the disclosure, the T-shaped housing channel comprises a top portion comprising two shelf surfaces extending outward from the base portion, wherein the T-shaped slider housing comprises two top spars each comprising a spar contact surface configured to selectively engage with one of the two shelf surfaces, wherein a height of each of the two top spars is less than a height of the top portion of the T-shaped housing channel, and wherein the T-shaped slider housing is configured to move up and down within the T-shaped housing channel.

In one or more embodiments according to the disclosure, a method of operating a flow regulation clamp assembly comprises: disposing an intravenous tube within a flow regulation clamp assembly by extending the intravenous tube through a length of a base portion of a T-shaped housing channel disposed within a housing; turning a rotation knob coupled to the housing in a first rotational direction, thus turning a threaded engagement member of the rotation knob in the first rotation direction, the threaded engagement member engaged with a threaded slider bore of a T-shaped slider disposed within the T-shaped housing channel; moving a base spar of the T-shaped slider downward into the base portion of the T-shaped housing channel a defined linear distance of travel associated with a degree of rotation of the rotation knob; and pushing a contact surface of the base spar into the intravenous tube the defined linear distance of travel, thus occluding the intravenous tube a defined amount associated with a defined reduced fluid flow rate through the intravenous tube.

In aspects of the disclosure, the method further comprises: maintaining a self-locking engagement position of the base spar against the intravenous tube based on a frictional force between the threaded engagement member and the threaded slider bore being greater than a helical sliding tendency between the threaded engagement member and the threaded slider bore due to fluid forces pushing the intravenous tube against the slider, wherein each of the threaded engagement member and the threaded slider bore comprises square shaped threads configured so that a lead angle of the threading is less than a friction angle of the threading.

It is understood that any specific order or hierarchy of blocks in the methods of processes disclosed is an illustration of example approaches. Based upon design or implementation preferences, it is understood that the specific order or hierarchy of blocks in the processes may be rearranged, or that all illustrated blocks be performed. In some implementations, any of the blocks may be performed simultaneously.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, operations or processes disclosed is an illustration of exemplary approaches. Based upon design preferences, it is understood that the specific order or hierarchy of steps, operations or processes may be rearranged. Some of the steps, operations or processes may be performed simultaneously. Some or all of the steps, operations, or processes may be performed automatically, without the intervention of a user. The accompanying method claims, if any, present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A flow regulation clamp assembly comprising:

a housing having an open-ended boxlike structure and comprising:

a T-shaped housing channel disposed through a length of the housing with a top wide portion of the T-shaped housing channel disposed adjacent a top of the housing; and a knob base disposed on an outer portion of a top surface of the housing and comprising a base bore extending through the knob base into the top wide portion of the T-shaped housing channel;

a slider disposed in the housing channel, the slider comprising:

a T-shaped slider housing configured to slidingly move up and down within the T-shaped housing channel perpendicularly to the length of the housing; and a slider bore extending through at least a portion of a top wide portion of the T-shaped slider housing; and a rotation knob coupled to the knob base, the rotation knob comprising an engagement member disposed through the base bore of the housing and received by the slider bore of the slider, wherein rotation of the rotation knob in a first rotational direction is configured to cause the engagement member to push the entire T-shaped slider housing downward within the T-shaped housing channel and rotation of the rotation knob in a second rotational direction is configured to cause the engagement member to pull the entire T-shaped slider housing upward within the T-shaped housing channel.

2. The flow regulation clamp assembly of claim 1, wherein a base portion of the T-shaped housing channel comprises two opposing side walls and a bottom wall that collectively define a tube channel configured to receive an intravenous tube.

3. The flow regulation clamp assembly of claim 2, wherein the T-shaped slider housing comprises a base spar configured to slidingly fit into the tube channel, the base spar comprising a contact surface configured to engage the intravenous tube.

4. The flow regulation clamp assembly of claim 2, wherein the T-shaped housing channel comprises a top portion comprising two shelf surfaces extending outward from the base portion.

5. The flow regulation clamp assembly of claim 4, wherein the T-shaped slider housing comprises two top spars each comprising a spar contact surface configured to selectively engage with one of the two shelf surfaces.

6. The flow regulation clamp assembly of claim 5, wherein a height of each of the two top spars is less than a height of the top portion of the T-shaped housing channel.

7. The flow regulation clamp assembly of claim 1, wherein the T-shaped housing channel comprises a stop member configured to:

prevent the T-shaped slider from slidably moving further along the T-shaped housing channel; and to align the base bore and the slider bore.

8. The flow regulation clamp assembly of claim 1, wherein the knob base comprises at least one retention member configured to engage with a base portion of the rotation knob to keep the rotation knob movably coupled to the knob base.

9. The flow regulation clamp assembly of claim 8, wherein the at least one retention member comprises opposing flexible clamps each having a securing portion that overhangs a portion of the base portion of the rotation knob.

10. The flow regulation clamp assembly of claim 1, wherein the knob base comprises a plurality of scale markings disposed on a viewable surface of the knob base, the scale markings configured to indicate levels of occlusion of an intravenous tube disposed within the T-shaped housing channel, each level of occlusion associated with a fluid flow rate through the intravenous tube.

11. The flow regulation clamp assembly of claim 1, wherein each of the engagement member of the rotation knob and the slider bore is threaded, wherein rotation of the engagement member in a first direction within the slider bore causes the T-shaped slider housing to move upward within the T-shaped housing channel, and wherein rotation of the engagement member in a second direction within the slider bore causes the T-shaped slider housing to move downward within the T-shaped housing channel.

12. The flow regulation clamp assembly of claim 11, wherein a specific degree of rotation of the rotation knob in the first direction is configured to cause upward travel of the T-shaped slider housing a specific linear distance, and wherein the specific degree of rotation of the rotation knob in the second direction is configured to cause downward travel of the T-shaped slider housing the specific linear distance.

13. The flow regulation clamp assembly of claim 11, wherein threading of each of the engagement member and the slider bore comprises square shaped threads configured so that a lead angle of the threading is less than a friction angle of the threading.

14. The flow regulation clamp assembly of claim 13, wherein the slider is configured to be self-locking by maintaining an engagement position against an intravenous tube disposed within the T-shaped housing channel based on a frictional force between the engagement member and the slider bore being greater than a helical sliding tendency between the engagement member and the slider bore due to fluid forces pushing the intravenous tube against the slider.

15. The flow regulation clamp assembly of claim 13, wherein a pitch of the square shaped threads is configured so that one revolution of the rotation knob equates to a linear distance required for the slider to move downward to compress an intravenous tube fully closed.

16. An infusion set comprising:

a drip chamber;

an intravenous tube; and the flow regulation clamp assembly of claim 1.

17. The infusion set of claim 16, wherein each of the engagement member of the rotation knob and the slider bore comprises square shaped threads configured so that a lead angle of the threading is less than a friction angle of the threading, wherein the slider is configured to be self-locking by maintaining an engagement position against the intravenous tube based on a frictional force between the engagement member and the slider bore being greater than a helical sliding tendency between the engagement member and the slider bore due to fluid forces pushing the intravenous tube against the slider.

18. The infusion set of claim 16, wherein the T-shaped housing channel comprises a top portion comprising two shelf surfaces extending outward from a base portion, wherein the T-shaped slider housing comprises two top spars each comprising a spar contact surface configured to selectively engage with one of the two shelf surfaces, wherein a height of each of the two top spars is less than a height of the top portion of the T-shaped housing channel, and wherein the T-shaped slider housing is configured to move up and down within the T-shaped housing channel.

19. A method of operating the flow regulation clamp assembly of claim 1, the method comprising:

disposing an intravenous tube within the flow regulation clamp assembly by extending the intravenous tube through a length of a base portion of the T-shaped housing channel disposed within the housing;

turning the rotation knob coupled to the housing in the first rotational direction, thus turning a threaded portion of the engagement member of the rotation knob in the first rotation direction, the threaded portion of the engagement member engaged with a threaded portion of the slider bore of the T-shaped slider disposed within the T-shaped housing channel;

moving a base spar of the T-shaped slider downward into the base portion of the T-shaped housing channel a defined linear distance of travel associated with a degree of rotation of the rotation knob; and pushing a contact surface of the base spar into the intravenous tube the defined linear distance of travel, thus occluding the intravenous tube a defined amount associated with a defined reduced fluid flow rate through the intravenous tube.

20. The method of claim 19, further comprising:

maintaining a self-locking engagement position of the base spar against the intravenous tube based on a frictional force between the threaded portion of the engagement member and the threaded portion of the slider bore being greater than a helical sliding tendency between the threaded portion of the engagement member and the threaded portion of the slider bore due to fluid forces pushing the intravenous tube against the slider, wherein each of the threaded portion of the engagement member and the threaded portion of the slider bore comprises square shaped threads configured so that a lead angle of the threading is less than a friction angle of the threading.

* * * * *